(12) United States Patent
Gassivi et al.

(10) Patent No.: US 9,216,054 B2
(45) Date of Patent: Dec. 22, 2015

(54) ESOPHAGEAL MUCOSECTOMY SYSTEMS, DEVICES AND METHODS

(75) Inventors: Stephen D. Gassivi, Rochester, MN (US); Dennis A. Wigle, Rochester, MN (US)

(73) Assignee: Mayo Foundation for Medical Education and Research, Rochester, MN (US)

(*) Notice: Subject to any disclaimer, the term of this patent is extended or adjusted under 35 U.S.C. 154(b) by 843 days.

(21) Appl. No.: 13/289,541

(22) Filed: Nov. 4, 2011

(65) Prior Publication Data

US 2012/0143188 A1    Jun. 7, 2012

Related U.S. Application Data

(60) Provisional application No. 61/410,218, filed on Nov. 4, 2010.

(51) Int. Cl.
*A61B 18/14* (2006.01)
*A61B 17/3203* (2006.01)
*A61B 17/04* (2006.01)
*A61B 17/00* (2006.01)
*A61B 18/00* (2006.01)
*A61B 18/02* (2006.01)
*A61N 7/02* (2006.01)

(52) U.S. Cl.
CPC ......... *A61B 18/1492* (2013.01); *A61B 17/3203* (2013.01); *A61B 17/0401* (2013.01); *A61B 2017/00269* (2013.01); *A61B 2018/0022* (2013.01); *A61B 2018/00267* (2013.01); *A61B 2018/00488* (2013.01); *A61B 2018/00577* (2013.01); *A61B 2018/00595* (2013.01); *A61B 2018/0212* (2013.01); *A61B 2018/1467* (2013.01); *A61B 2018/1497* (2013.01); *A61B 2217/007* (2013.01); *A61B 2218/002* (2013.01); *A61N 7/022* (2013.01)

(58) Field of Classification Search
None
See application file for complete search history.

(56) References Cited

U.S. PATENT DOCUMENTS

| | | | |
|---|---|---|---|
| 6,053,913 | A | 4/2000 | Tu et al. |
| 6,551,310 | B1 | 4/2003 | Ganz et al. |
| 7,025,762 | B2 | 4/2006 | Johnston et al. |
| 7,530,979 | B2 | 5/2009 | Ganz et al. |
| 7,993,336 | B2 | 8/2011 | Jackson et al. |
| 8,398,631 | B2 | 3/2013 | Ganz et al. |
| 2003/0109870 | A1 | 6/2003 | Lee et al. |
| 2003/0129751 | A1 | 7/2003 | Grikscheit et al. |
| 2004/0249343 | A1 | 12/2004 | Cioanta |
| 2005/0013870 | A1 | 1/2005 | Freyman et al. |

(Continued)

FOREIGN PATENT DOCUMENTS

WO    2006/122414 A1    11/2006

OTHER PUBLICATIONS

Farrell et al., "Resection and advancement of esophageal mucosa," *Surgical Endoscopy*, 2001;15:937-941.

(Continued)

*Primary Examiner* — Brian T Gedeon
*Assistant Examiner* — Ankit Tejani
(74) *Attorney, Agent, or Firm* — Mueting, Raasch & Gebhardt, P.A.

(57) ABSTRACT

Systems, devices, apparatus and methods that may be used for en bloc circumferential esophageal mucosal resection or ablation that can extend over only a selected portion or all of the length of the esophagus.

20 Claims, 6 Drawing Sheets

(56) References Cited

U.S. PATENT DOCUMENTS

| | | | |
|---|---|---|---|
| 2005/0149081 A1 | 7/2005 | Ricota et al. | |
| 2005/0182438 A1* | 8/2005 | Scopton et al. | 606/194 |
| 2005/0287320 A1 | 12/2005 | Dalton et al. | |
| 2006/0095032 A1 | 5/2006 | Jackson et al. | |
| 2007/0038022 A1* | 2/2007 | Nakao | 600/104 |
| 2007/0066869 A1* | 3/2007 | Hoffman | 600/121 |
| 2007/0166396 A1 | 7/2007 | Badylak et al. | |
| 2008/0207994 A1* | 8/2008 | Gonon | 600/104 |
| 2008/0275550 A1 | 11/2008 | Kheradvar et al. | |
| 2010/0125272 A1* | 5/2010 | Scopton et al. | 606/46 |

OTHER PUBLICATIONS

France et al., "Use of ethylenediaminetetraacetic acid for in vivo stripping of columnar mucosa: pilot study in an experimental model," *ANZ J. Surg.*, 2006;76:392-397.

Macchiarini et al., "Clinical transplantation of a tissue-engineered airway," *The Lancet*, 2008;372:2023-2030.

Nakase et al., "Intrathoracic esophageal replacement by in situ tissue-engineered esophagus," *J. Thoracic Cardio. Surg.*, 2008;136(4):850-859.

Nieponice et al., "An extracellular matrix scaffold for esophageal stricture prevention after circumferential EMR," *Gastrointestinal Endoscopy*, 2009;69(2):289-296.

Rajan et al., "Widespread Endoscopic Mucosal Resection of the Esophagus with Strategies for Stricture Prevention: A Preclinical Study," *Endoscopy*, 2005;37:1111-1115.

Saito et al., "Usefulness of biodegradable stents constructed of poly-/-lactic acid monofilaments in patients with benign esophageal stenosis," *World J. of Gastroenterol.*, 2007;13(29):3977-3980.

Willingham et al., "En bloc esophageal mucosectomy for concentric circumferential mucosal resection," *Gastrointestinal Endoscopy*, 2009;69:147-151.

Witteman et al., "Transoral Endoscopic Inner Layer Esophagectomy: Management of High-Grade Dysplasia and Superficial Cancer with Organ Preservation," *J. Gastrointestinal Surgery*, 2009;13:2104-2112.

* cited by examiner

ESOPHAGEAL MUCOSECTOMY SYSTEMS, DEVICES AND METHODS

RELATED APPLICATION

This application claims the benefit under 35 U.S.C. §119 (e) of U.S. Provisional Patent Application No. 61/410,218, filed Nov. 4, 2010 and titled ESOPHAGEAL MUCOSECTOMY SYSTEMS, DEVICES AND METHODS, which is hereby incorporated by reference in its entirety.

Systems, devices and methods for performing esophageal mucosectomy procedures are described herein.

Esophagectomy is standard treatment for Barrett's esophagus with high grade dysplasia and malignancy. However, due to high morbidity rates associated with esophageal resection, techniques have been developed that remove only the involved regions in an attempt to preserve the esophagus. Those techniques may include, for example, endoscopic mucosal resection (EMR) and radiofrequency (RF) ablation. In many instances, however, those techniques do not reliably or consistently remove all lesions from the esophagus.

Examples of some approaches to treating involved regions of the esophagus may be described in, e.g., US Patent Publication Nos. US 2002/0143323 (Johnston et al.); US 2006/0095032 (Jackson et al.); and US 2009/0048593 (Ganz et al.); as well as in U.S. Pat. No. 6,551,310 (Ganz et al.). Further approaches may be described in, e.g., Willingham et al., *En bloc esophageal mucosectomy for concentric circumferential mucosal resection*, Gastrointestinal Endoscopy 2009; 69 (1): 147-151; Nieponice et al., *An extracellular matrix scaffold for esophageal stricture prevention after circumferential EMR*, Gastrointestinal Endoscopy 2009; 69 (2): 289-296; Nakase et al., *Intrathoracic esophageal replacement by in situ tissue-engineered esophagus*, The Journal of Thoracic and Cardiovascular Surgery (October 2008); 136 (4): 850-859; Saito et al., *Usefulness of biodegradable stents constructed of poly-/-lactic acid monofilaments in patients with benign esophageal stenosis*, World J. Gastroenterol. 13(29): 3977-3980 (Aug. 7, 2007); Rajan et al., *Widespread Endoscopic Mucosal Resection of the Esophagus with Strategies for Stricture Prevention: A Preclinical Study*, Endoscopy 2005; 37 (11): 111-1115; Macchiarini et al., *Clinical transplantation of a tissue-engineered airway*, Lancet 2008; 372: 2023-30; Farrell et at, *Resection and advancement of esophageal mucosa*, Surg. Endosc. 2001; 15: 937-941; Witteman et al., *Transoral Endoscopic Inner Layer Esophagectomy: Management of High-Grade Dysplasia and Superficial Cancer with Organ Preservation*, J. Gastrointest. Surg. (2009) 13: 2104-2112; and France et al., *Use of ethylenediaminetetraacetic acid for in vivo stripping of columnar mucosa*, ANZ J. Surg. 2006; 76: 392-397.

SUMMARY

The systems, devices, apparatus and methods described herein may preferably be used for en bloc circumferential esophageal mucosal resection or ablation that can extend over only a selected portion or all of the length of the esophagus.

In some embodiments, the systems, devices and methods described herein involve a mechanical approach in which the mucosal layer is removed from the underlying submucosal layer with the process beginning at a selected location in the esophagus and extending distally towards the GE junction/stomach or beginning at a selected location in the esophagus and extending proximally away from the GE junction/stomach. Tissue engineering/regenerative medicine techniques can be used to reduce the likelihood of stricture formation as a result of the esophageal mucosectomy.

In some embodiments, the systems, devices and methods described herein involve an electrical approach in which the mucosal layer is ablated using an expandable device that positions ablation electrodes in contact with the mucosal tissue in the esophagus, followed by deployment of a scaffold that can be used to deliver tissue engineering/regenerative medicine therapy to reduce the likelihood of stricture formation as a result of the esophageal mucosectomy.

In a first aspect, some embodiments of the esophageal mucosectomy systems described herein may include a mucosectomy device that includes a body having a proximal end and distal end, wherein a longitudinal axis extends between the proximal end and the distal end, a cauterizing ring located at the distal end of the body, the cauterizing ring capable of separating mucosal tissue from submucosal tissue about the circumference of the esophagus as the distal end of the mucosectomy device is advanced therethrough, and expandable support structure supporting the cauterizing ring, wherein the support structure is expandable from a delivery configuration to a deployed configuration, wherein the diameter of the cauterizing ring is larger in the deployed configuration than in the delivery configuration, and further wherein the body of the mucosectomy device is narrower at the proximal end than support structure when the support structure is in the deployed configuration. The systems may, in some embodiments, include an optional dissection device configured to dissect mucosal tissue in circumferential direction at a selected location within an esophagus, wherein the dissected mucosal tissue forms a free end of mucosal tissue separated from submucosal tissue, and an optional mucosal tissue retention apparatus configured to retain the free end of mucosal tissue.

In some embodiments of the first aspect of the systems described herein, the mucosal tissue retention apparatus comprises suture material.

In some embodiments of the first aspect of the systems described herein, the mucosal tissue retention apparatus comprises tissue clips.

In some embodiments of the first aspect of the systems described herein, the cauterizing ring of the mucosectomy device comprises two or more independent cauterizing sections, wherein cauterizing energy can be selectively delivered to one or more of the cauterizing sections.

In some embodiments of the first aspect of the systems described herein, the mucosectomy device further comprises a delivery port located proximal the distal end of the mucosectomy device, wherein the delivery port is in fluid communication with a lumen that extends to the proximal end of the mucosectomy device, whereby a fluid can be delivered through the lumen to the delivery port where it exits the mucosectomy device.

In some embodiments of the first aspect of the systems described herein, the support structure of the mucosectomy device comprises an inflatable bladder.

In some embodiments of the first aspect of the systems described herein, the support structure of the mucosectomy device comprises a coiled ring.

In some embodiments of the first aspect of the systems described herein, the support structure of the mucosectomy device comprises a plurality of panels, wherein each panel of the plurality of panels comprises a cauterizing surface at a distal end of the panel.

In some embodiments of the first aspect of the systems described herein, the system further comprises a scaffold located over an exterior surface of the body of the mucosectomy device, wherein the scaffold comprises a distal end that is located proximal from the distal end of the mucosectomy device, and wherein the scaffold is expandable from a delivery configuration to a deployed configuration, wherein the diameter of the scaffold is larger in the deployed configuration than in the delivery configuration. In some embodiments, the support structure is collapsible from the deployed configuration to a removal configuration, wherein the diameter of the support structure is smaller in the collapsed configuration than in the deployed configuration, and further wherein the scaffold comprises an internal passage in its deployed configuration that is larger than the support structure in its collapsed configuration such that the distal end of the mucosectomy device can be withdrawn proximally through the internal passage of the scaffold when the support structure is in its collapsed configuration.

In a second aspect, some embodiments of the esophageal mucosectomy devices described herein may include a body having a proximal end and distal end, wherein a longitudinal axis extends between the proximal end and the distal end, a cauterizing ring located at the distal end of the body, the cauterizing ring capable of separating mucosal tissue from submucosal tissue about the circumference of the esophagus as the distal end of the mucosectomy device is advanced therethrough, and expandable support structure supporting the cauterizing ring, wherein the support structure is expandable from a delivery configuration to a deployed configuration, wherein the diameter of the cauterizing ring is larger in the deployed configuration than in the delivery configuration, and further wherein the body of the mucosectomy device is narrower at the proximal end than support structure when the support structure is in the deployed configuration.

In some embodiments of the second aspect of the devices described herein, the cauterizing ring of the mucosectomy device comprises two or more independent cauterizing sections, wherein cauterizing energy can be selectively delivered to one or more of the cauterizing sections.

In some embodiments of the second aspect of the devices described herein, the mucosectomy device further comprises a delivery port located proximal the distal end of the mucosectomy device, wherein the delivery port is in fluid communication with a lumen that extends to the proximal end of the mucosectomy device, whereby a fluid can be delivered through the lumen to the delivery port where it exits the mucosectomy device.

In a third aspect, some embodiments of the esophageal mucosectomy devices described herein may include a body having a proximal end and distal end, wherein a longitudinal axis extends between the proximal end and the distal end, a tissue separation ring located at the distal end of the body, the tissue separation ring comprising a plurality of ports configured to deliver jets of liquid capable of separating mucosal tissue from submucosal tissue about the circumference of the esophagus as the distal end of the mucosectomy device is advanced therethrough, and expandable support structure that is expandable from a delivery configuration to a deployed configuration, wherein the diameter of the tissue separation ring is larger in the deployed configuration than in the delivery configuration, and further wherein the body of the mucosectomy device is narrower at the proximal end than support structure when the support structure is in the deployed configuration.

In some embodiments of the third aspect of the devices described herein, the expandable support structure may comprise a plurality of panels.

In a fourth aspect, some embodiments of the esophageal mucosectomy systems described herein may include an expandable ablation body comprising ablation electrodes positioned on an exterior surface of the ablation body, wherein the ablation body comprises a distal end and a proximal end, with a longitudinal axis extending from the distal end to the proximal end; a generally tubular delivery sheath located within an interior of the ablation body, wherein the delivery sheath is located between the proximal end and the distal end of the ablation body; and a scaffold restrained within an interior of the delivery sheath, wherein the scaffold is expandable to a deployed configuration when not restrained by the delivery sheath, wherein the scaffold comprises a diameter in its deployed configuration that is larger than its diameter when restrained within the delivery sheath.

In some embodiments of the fourth aspect of the systems described herein, the scaffold is electrically isolated from the electrical energy delivered to the ablation electrodes when the scaffold is restrained within the delivery sheath.

In some embodiments of the fourth aspect of the systems described herein, the ablation body is expandable from a delivery configuration to an ablation configuration, wherein the outer diameter of the ablation body is larger in the ablation configuration than in the delivery configuration, and further wherein the exterior surface of the ablation body facilitates physical contact between the ablation electrodes and mucosal tissue when the ablation body is expanded to the ablation configuration inside an esophagus.

In some embodiments of the fourth aspect of the systems described herein, the system further comprises ejection apparatus that ejects the scaffold from the delivery sheath such that scaffold can be ejected from the delivery sheath as the ablation body is withdrawn proximally.

In a fifth aspect, some embodiments of methods of performing an esophageal mucosectomy are described herein, the methods comprising using an esophageal mucosectomy device and/or system as described herein for en bloc circumferential esophageal mucosal resection of the mucosal tissue layer in a selected portion of an esophagus.

The above summary is not intended to describe each embodiment or every implementation of the systems, devices, apparatus and methods described herein. Rather, a more complete understanding of the systems, devices, apparatus and methods described herein will become apparent and appreciated by reference to the following Description of Illustrative Embodiments and claims in view of the accompanying figures of the drawing.

DESCRIPTION OF ILLUSTRATIVE EMBODIMENTS

Figure 1:
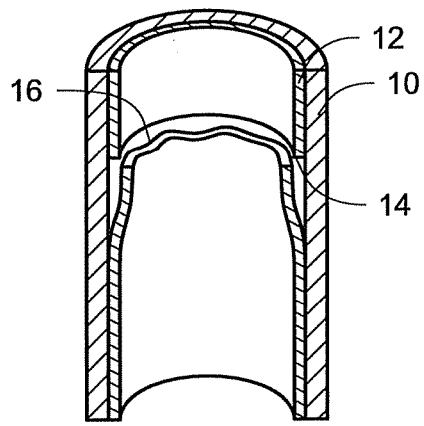
FIG. 1 is a cross-sectional view of a portion of an esophagus after dissection of the submucosa to provide partial separation of the mucosal layer from the submucosa.

In the following description of illustrative embodiments, reference is made to the accompanying figures of the drawing which form a part hereof, and in which are shown, by way of illustration, specific embodiments that may be practiced. It is to be understood that other embodiments may be utilized and structural changes may be made without departing from the scope of the present invention.

The esophageal mucosectomy systems described herein may preferably be deployed through an overtube that is provided as a part of the apparatus/devices supplied with the system or through a working channel of an endoscope. The procedures may, in some embodiments, be conducted under direct visualization (e.g., via an endoscopic camera, a camera incorporated into the mucosectomy devices/apparatus described herein and/or an overtube, using a separate camera deployed through an overtube or a working channel in an endoscope, etc.).

In the mechanical approach described herein, the mucosal layer is separated from the underlying submucosal layer at a selected location circumferentially around the esophagus. Circumferential dissection of the mucosal layer may be performed using any suitable technique, e.g., endoscopic cap dissection, cautery, probe scissors, etc.

Figure 4:
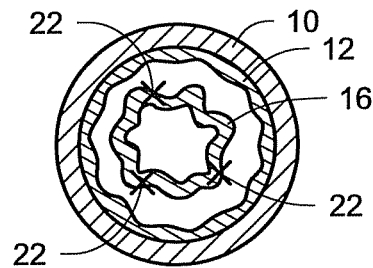
FIG. 4 is a view taken distally down the esophagus of FIG. 3 with a portion of the retention apparatus and all of the mucosectomy device removed for clarity, with FIG. 4 depicting the free edge 16 of the mucosal layer 12.

The circumferential dissection of the mucosal layer creates a starting point for the mucosectomy device as described herein. Referring to FIG. 2, a portion of an esophagus is depicted with the submucosa 12b underlying the mucosal layer 12a (depicted together as layer 12 in FIGS. 1 and 4). The muscularis mucosa 10a surrounds the submucosa 12b and is, in turn, surrounded by the muscularis propria 10b (with the muscularis mucosa 10a and muscularis propria 10b depicted together as layer 10 in FIGS. 1 and 4). The circumferential dissection is performed at selected location 14 and preferably creates a free edge 16 for the mucosal layer 12a by separating the submucosa 12b that underlies the mucosal layer 12a.

Circumferential dissection of the mucosal layer can be performed at one end of the portion over which the esophageal mucosectomy is to be performed with the mucosectomy being advanced towards the opposite end followed by dissection of the mucosal layer when the mucosectomy has reached the opposite end. Alternatively, a circumferential dissection of the mucosal layer may be performed at both ends of the portion over which the esophageal mucosectomy is to be performed before the mucosal layer is removed as discussed herein.

Figure 2:
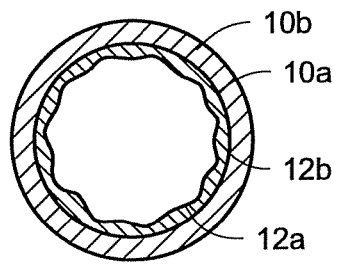
FIG. 2 is a cross-sectional view of the esophagus of FIG. 1 depicting the arrangement of the mucosal layer relative to the submucosal, the muscularis mucosa and the muscularis propria.

After a circumferential free edge 16 of the mucosal layer 12a has been formed as seen in FIG. 1, a mucosal tissue retention apparatus configured to retain the free end 16 of mucosal tissue may be attached to the free end 16. The mucosal tissue retention apparatus may take any suitable form capable of securely grasping/retaining the mucosal layer 12a proximate the free edge 16.

Figure 3:
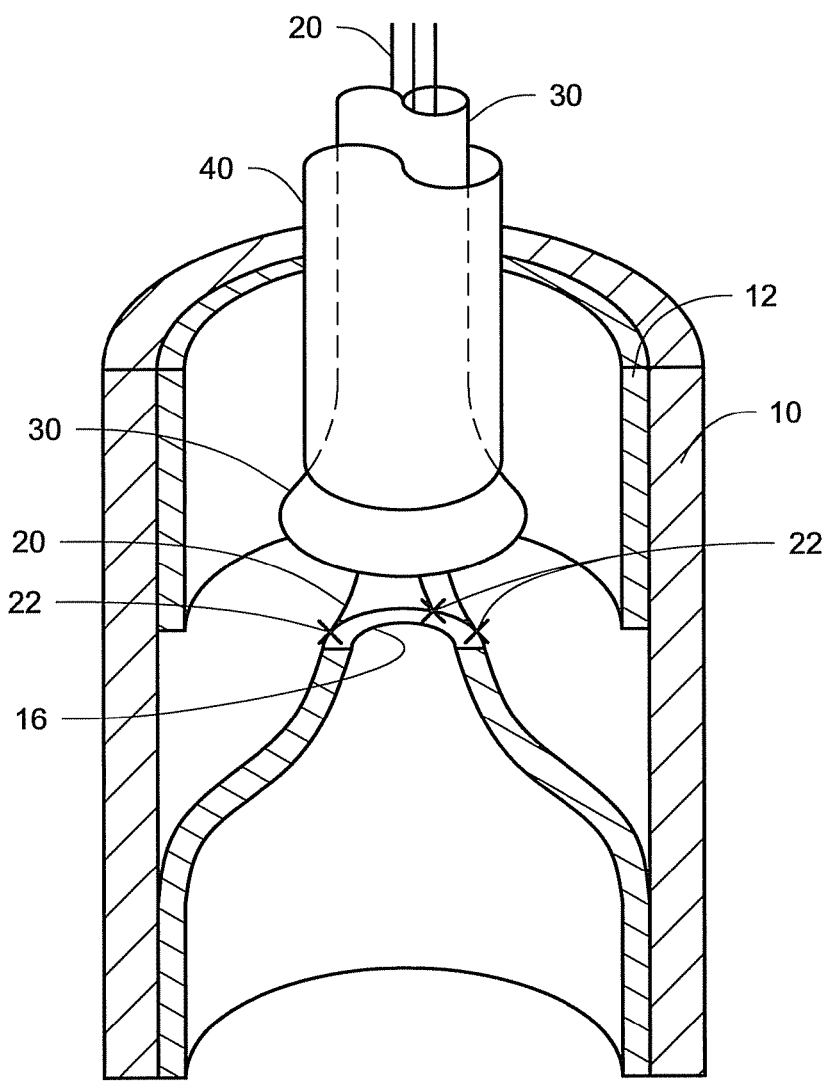
FIG. 3 is a partial cross-sectional view of FIG. 1 after retention of the free edge of the dissected mucosal layer and advancement of one embodiment of a mucosectomy device as described herein.

Referring to FIG. 3, one embodiment of a retention apparatus may take the form of a plurality of suture lines 20 (or other structures capable of providing tensile force to draw the mucosal layer 12a proximally) that are attached to the mucosal layer 12a at connections 22 by any suitable technique, e.g., clips, t-tags, suture locations, etc. In the embodiment depicted in FIGS. 3 and 4, the suture lines 20 are attached to the mucosal layer 12a by connections 22 in the form of sutures.

FIG. 3 also depicts a mucosectomy device 30 contained in a sheath 40 (e.g., an overtube, endoscope, etc.) during delivery into the esophagus. The mucosectomy device 30 is depicted as expanding from its constrained delivery configuration within the sheath 40 towards a deployed configuration as described herein. The mucosectomy device 30 is being advanced towards the free edge 16 of the mucosal layer 12a and, in the depicted embodiment, the suture lines 20 of the tissue retention apparatus extend proximally from connections 22 through the mucosectomy device 30.

As described herein, some embodiments of the mucosectomy devices may preferably include a body having a proximal end and distal end, wherein a longitudinal axis extends between the proximal end and the distal end. A cauterizing ring may preferably be located at the distal end of the body of the mucosectomy device. The cauterizing ring is preferably capable of separating mucosal tissue from submucosa about the circumference of the esophagus as the distal end of the mucosectomy device is advanced through esophagus (either distally or proximally as discussed herein).

Although the cauterizing ring may, in some embodiments, a continuous circular article, the ring may also take any other shape, e.g., oval, elliptical, octagonal, etc. In addition, the cauterizing ring may be delivered in a collapsed configuration (in, e.g., a sheath, endoscope channel, etc.) that expands when deployed at a selected location. Furthermore, the cauterizing portions of the cauterizing may extend continuously around the cauterizing ring in some embodiments. In other embodiments, only portions of the ring may cauterize tissue, e.g., the cauterizing ring may include one or more cauterizing segments positioned about the ring (see, e.g., FIG. 5 and the corresponding discussion herein).

The mucosectomy devices may, in some embodiments, further include an expandable support structure supporting the cauterizing ring. The support structure may preferably be expandable from a delivery configuration to a deployed configuration, wherein the diameter of the cauterizing ring is larger in the deployed configuration than in the delivery configuration. In addition, the body of the mucosectomy device may be narrower at the proximal end than support structure when the support structure is in the deployed configuration.

Figure 5:
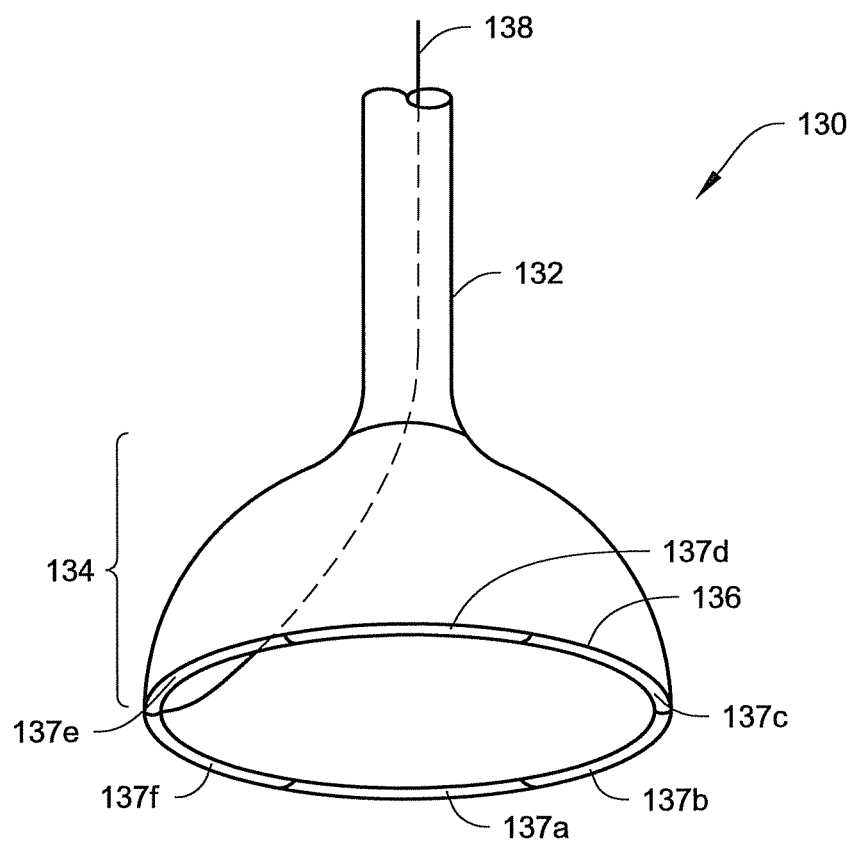
FIG. 5 depicts one embodiment of a mucosectomy device as described herein.
Figure 6:
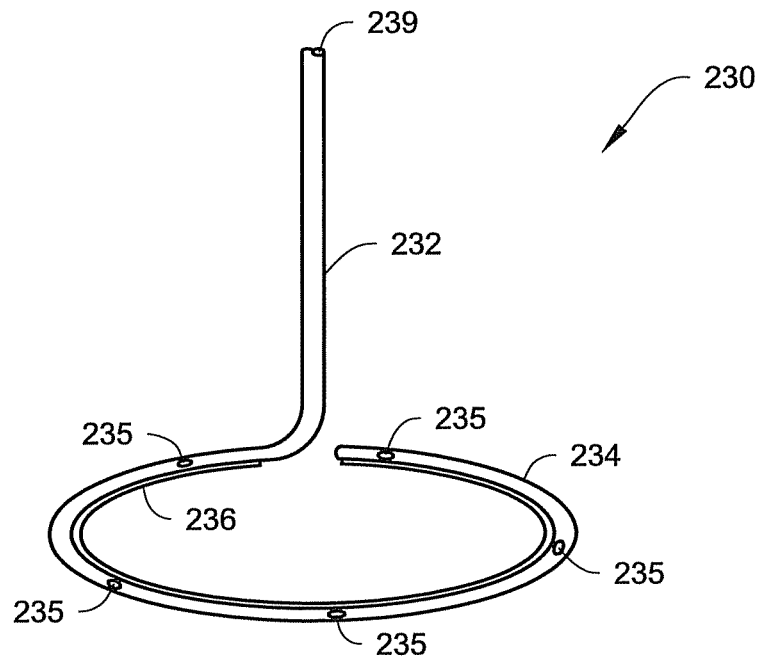
FIG. 6 depicts another embodiment of a mucosectomy device as described herein.
Figure 7:
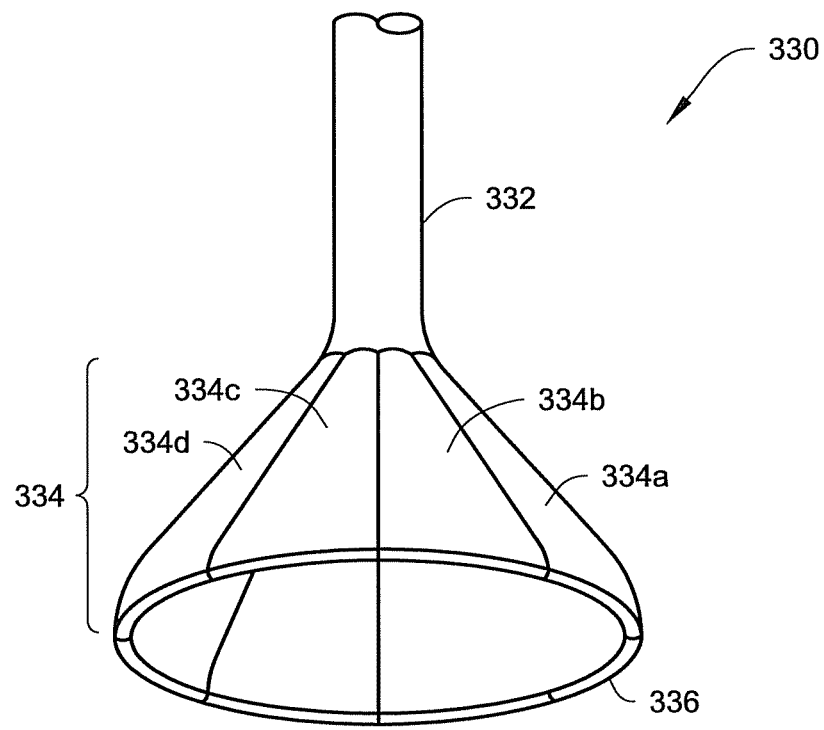
FIG. 7 depicts another embodiment of a mucosectomy device as described herein.

Various illustrative embodiments of mucosectomy devices are depicted in FIGS. 5-7. The mucosectomy device 130 depicted in FIG. 5 includes, for example, a body 132 and an expandable support structure 134 located at the distal end of the body 132. The expandable support structure 134 may include, e.g., one or more inflatable bladders and/or other structures that are capable of being transformed from a delivery configuration to a deployed configuration as described herein. The support structure 134 is depicted in the deployed configuration in FIG. 5. In the delivery configuration, the support structure may preferably have a size (e.g., diameter) that is closer to the size of the body 132 of the mucosectomy device 130.

The mucosectomy device 130 of FIG. 5 also preferably includes a cauterizing ring 136 positioned at the distal end of the body 132, with the cauterizing ring 136 being used during advancement of the mucosectomy device 130 to facilitate separation of the mucosal tissue layer from the underlying submucosal tissue.

In some embodiments in which energy (e.g., Radio Frequency (RF), ultrasonic, cautery, cryogenic, etc.) may be used to assist with separation of the submucosal tissue such that a mucosal tissue layer can be formed as described herein. In some embodiments, the energy may be delivered intermittently (e.g., the energy could be delivered followed by advancement of the mucosectomy device). In some embodiments, the energy could be delivered at the same time as the mucosectomy device is advancing. In still other embodiments, the mucosectomy device may be designed to separate the submucosal tissue layer mechanical techniques alone, e.g., a mucosectomy device may have a tapered edge or wedge-like design that separates the submucosal tissue as the mucosectomy device is advanced.

In some embodiments, the cauterizing ring 136 may include two or more independent cauterizing sections. In the embodiment depicted in FIG. 5, the cauterizing ring includes six cauterizing sections denoted by reference numbers 137a-137f. In such an embodiment, it may be preferred that cauterizing energy can be selectively delivered to one or more of the cauterizing sections. Although not depicted in FIG. 5, the mucosectomy device 130 may include a plurality of leads extending to the proximal end of the body 132, with the leads capable of delivering to electrical energy to the cauterizing sections.

The embodiment of a mucosectomy device 130 depicted in FIG. 5 may also includes a suture loop or ring integrated into the support structure 134, with the suture loop or ring being useful as a tissue retention apparatus in conjunction with the mucosectomy device 130. In the depicted embodiment, the suture loop/ring is located proximate the cauterizing ring 136 and includes a proximally extending component 138 that can potentially be used to tighten the suture loop and/or ring on the mucosal tissue in place of the connections 22 in the form of clips or sutures (as depicted and discussed in connection with FIG. 3).

In the embodiment depicted in FIG. 5, the support structure 134 can be used to position the suture loop/ring 136 around the free end of the mucosal tissue such that it can be pulled taut. With the suture loop/ring 136 attached to the mucosal tissue, the support structure 134 may be used to push/separate the mucosal layer from the submucosa while the suture ring/loop 136 holds the mucosal layer proximate the free edge of the mucosal layer. In that manner, the support structure 134 would move away from the suture loop/ring 136 as the support structure is advanced through the submucosal.

Referring to FIG. 6, another embodiment of a mucosectomy device 230 may include a form similar to that depicted. The mucosectomy device 230 may include body 232 that terminates in a ring-like support structure 234. The ring-like support structure 234 preferably supports a cauterizing ring 236 that can be used to delivery cauterizing energy as a part of mucosectomy procedure.

The illustrative embodiment of the mucosectomy device 230 depicted in FIG. 6 also includes a plurality of delivery ports 235 that are located in the ring-like support structure 234. Although multiple delivery ports 235 are provided in the illustrative embodiment, mucosectomy devices may be provided with as few as one delivery port (or none). The delivery ports 235 may preferably be located proximal the distal end of the mucosectomy device 230 such that fluids containing drugs, etc. may be delivered before, during, and/or after a mucosectomy procedure. The delivery ports 235 are in fluid communication with a lumen 239 that extends to the proximal end of the mucosectomy device 230 through the body 232.

Examples of some potentially useful drugs or medications that could be delivered through the delivery ports of the depicted device or other devices may include, but are not limited to hemostatic agents, cytoprotective agents (e.g., sulcrate, etc.), local chemotherapeutics or other esophageal cancer therapeutics, growth factors or other agents to support stem cell or tissue growth, etc.

In those embodiments that provide for the delivery of medications and cauterizing energy during the mucosectomy, the cautery, medication delivery, and any other interventions may be applied as the mucosal tissue layer is removed from the selected portion of the esophagus.

In still other embodiments, the ports 235 on the mucosectomy device 230 may be configured to deliver liquid in the form of one or more liquid jets that facilitate separation of the mucosal tissue layer from the underlying submucosal tissue ring. In particular, liquid may be delivered through lumen 239 to ports 235 at pressures and/or velocities sufficient to separate the mucosal tissue layer from the underlying submucosal tissue. The liquid delivered may be saline, water, etc. In some embodiments, the liquid may include drugs or medications as described above. In some embodiments, the liquids may include particulate matter that may also facilitate separation of the mucosal tissue layer from the underlying submucosal tissue. The ports 235 may be provided in place of or in addition to the cauterizing ring 236. In other words, in some embodiments the liquid jets formed by the ports 235 may take the place of the cauterizing ring 236 for the separation of tissue, while in other embodiments, the liquid jets formed by the ports 235 may be used in addition to cauterizing energy for the separation of tissue.

Another illustrative embodiment of a mucosectomy device 330 is depicted in FIG. 7 and includes a body 332 and an expandable support structure 334 located at the distal end of the body 332. The expandable support structure 334 may, in this depicted embodiment, include, e.g., a plurality of panels (see, e.g., panels 334a-334d in FIG. 7). The panels may preferably overlap each other in the manner of, e.g., the petal of a flower. To reduce the size of the support structure 334, the overlap between the panels is increased. In some embodiments, each panel may include a cauterizing surface 336 at a distal end of the panel, such that the cauterizing surfaces 336 of the panels forms a cauterizing ring as described herein.

In still other embodiments, one or more of the panels 334a-334d of the expandable support structure 334 may include one or more ports that are configured to deliver liquid in the form of one or more liquid jets that facilitate separation of the mucosal tissue layer from the underlying submucosal tissue ring. The ports may, for example, be positioned proximate the edges of the panels 334a-334d in place of or near the cauterizing surfaces 336. In particular, liquid may be delivered through a lumen to ports on one or more of the panels 334a-334d at pressures and/or velocities sufficient to separate the mucosal tissue layer from the underlying submucosal tissue as described above in connection with the embodiment of FIG. 6. The ports may be provided in place of or in addition to the cauterizing surfaces 336. In other words, in some embodiments the liquid jets formed by the ports may take the place of the cauterizing surfaces 336 for the separation of tissue, while in other embodiments, the liquid jets may be used in addition to cauterizing energy for the separation of tissue.

Figure 8:
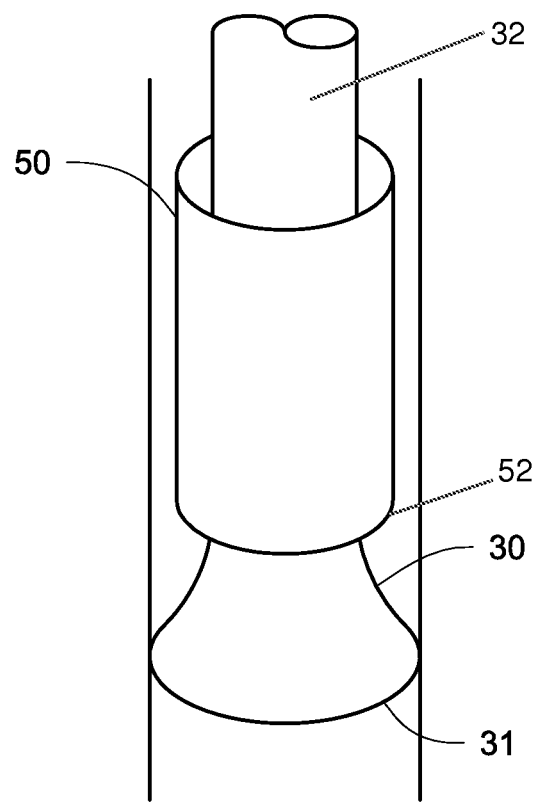
FIG. 8 depicts an embodiment of a mucosectomy system that includes a scaffold mounted on a mucosectomy device.

Referring to FIG. 8, an illustrative embodiment of mucosectomy system is depicted that includes a scaffold 50 located over an exterior surface of the body 32 of the mucosectomy device 30. The scaffold has a distal end 52 that is located proximal from the distal end 31 of the mucosectomy device 30. The scaffold 50 may preferably be expandable from a delivery configuration to a deployed configuration, wherein the diameter of the scaffold 50 is larger in the deployed configuration than in the delivery configuration. Transition from the delivery configuration to the deployed configuration for the scaffold 50 may be effected by a variety of structures, e.g., by an inflatable balloon, etc.

The scaffold 50 may be used to deliver tissue and/or medication therapies to an esophagus after or as a part of the mucosectomy procedure. The scaffold 50 may be in the form of, e.g., a stent and may be manufactured using materials and/techniques that are used for stents and similar articles (e.g., vascular grafts, etc.).

The use of tissue scaffolds and similar devices may be described in, e.g., U.S. Patent Publication Nos. US 2003/0129751 (Grikscheit et al.); US 2004/0249343 (Cionta); US 2005/0013870 (Freyman et al.); US 2005/0287320 (Dalton et al.); US 2007/0166396 (Badylak et al.); and US 2008/0275550 (Kheradvar et al.); as well as in International Publication No. WO 2006/122414 (Freier et al.). Further approaches that may be used in connection with the scaffolds described herein may be found in Nieponice et al., *An extracellular matrix scaffold for esophageal stricture prevention after circumferential EMR*, Gastrointestinal Endoscopy 2009; 69 (2): 289-296; Nakase et al., *Intrathoracic esophageal replacement by in situ tissue-engineered esophagus*, The Journal of Thoracic and Cardiovascular Surgery (October 2008); 136 (4): 850-859; Saito et al., *Usefulness of biodegradable stents constructed of poly-/-lactic acid monofilaments in patients with benign esophageal stenosis*, World J. Gastroenterol. 13(29): 3977-3980 (Aug. 7, 2007); and Rajan et al., *Widespread Endoscopic Mucosal Resection of the Esophagus with Strategies for Stricture Prevention: A Preclinical Study*, Endoscopy 2005; 37 (11): 111-1115.

In various embodiments of the mucosectomy devices described herein, the support structures may be collapsible from the deployed configuration to a removal configuration, wherein the diameter of the support structure is smaller in the collapsed configuration than in the deployed configuration. In those embodiments that include a scaffold, the scaffold may include an internal passage in its deployed configuration that is larger than the support structure in its collapsed configuration such that the distal end of the mucosectomy device can be withdrawn proximally through the internal passage of the scaffold when the support structure is in its collapsed configuration.

One illustrative method of using the embodiments of mucosectomy systems described in connection with FIGS. 1-8 may involve the following procedures. An overtube may be located in the patient's esophagus. The overtube may be coupled with a mouthguard/bite block as is known in the art. An endoscope may be introduced through the overtube to allow for visualization and measurement of features in the esophagus.

With a location selected, a circumferential submucosal dissection may be performed using any suitable technique, e.g., endoscopic cap dissection, cautery, probe scissors, etc.

Referring to FIGS. 9-13, various illustrative embodiments of an esophageal mucosectomy system are depicted and will be described. These embodiments rely on the use of electrical energy in contrast to the mechanical approaches of the systems described in connection with FIGS. 1-8.

Figure 9:
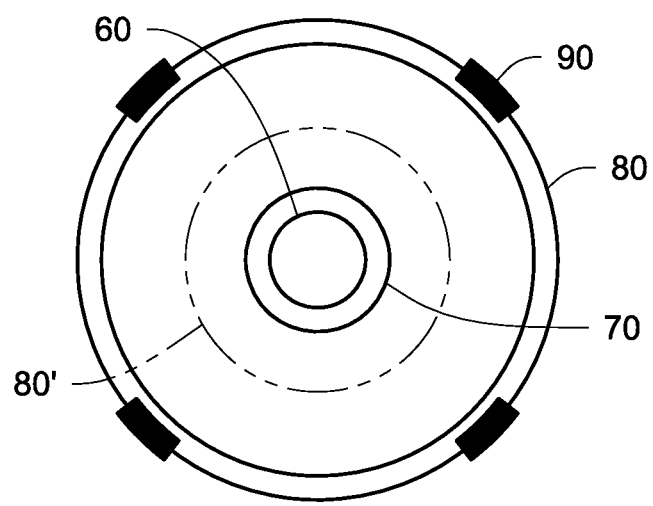
FIG. 9 is an end view of one embodiment of an esophageal mucosectomy system including an ablation body with a scaffold located therein.
Figure 11:
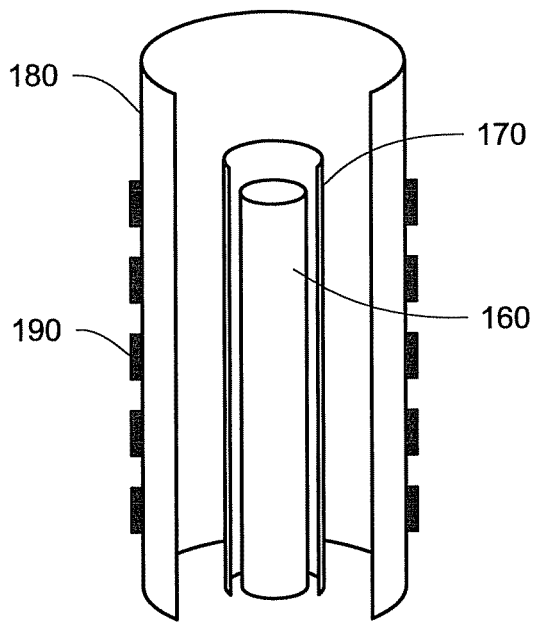
FIG. 11 depicts another embodiment of an esophageal mucosectomy system including an ablation body with a scaffold located therein.

FIG. 9 is an end view of one illustrative embodiment of an esophageal mucosectomy system which includes an inner scaffold 60 (e.g., a stent) constrained within a delivery sheath 70. An ablation body 80 surrounds the scaffold 60 and the delivery sheath 70. FIG. 11 is a perspective view of the system of FIG. 9, depicting the scaffold 60 located within the delivery sheath 70, which is, in turn, located in the ablation body 80.

In the illustrative embodiments described herein, the mucosectomy systems may include an expandable ablation body 80 that includes ablation electrodes 90 positioned on an exterior surface 86 of the ablation body 80. The ablation body comprises a distal end 84 and a proximal end 82, with a longitudinal axis 81 extending from the distal end 84 to the proximal end 82. The ablation body 80 is expandable from a delivery configuration (see, e.g., the ablation body 80' depicted in broken lines in FIG. 9) to an ablation configuration. The outer diameter of the ablation body 80 is larger in the ablation configuration than in the delivery configuration. The exterior surface 82 of the ablation body 80 facilitates physical contact between the ablation electrodes 90 and mucosal tissue in an esophagus when the ablation body 80 is expanded to the ablation configuration inside an esophagus.

Figure 10:
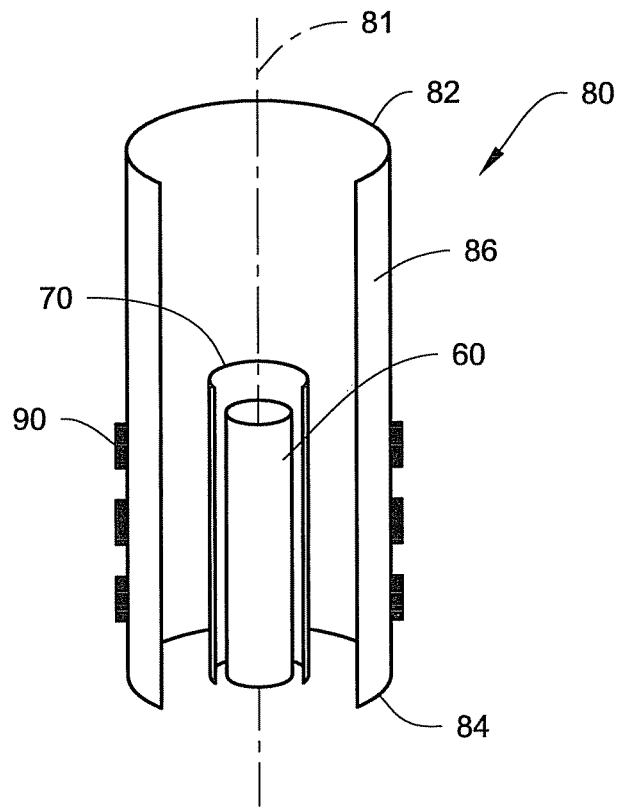
FIG. 10 depicts an embodiment of an esophageal mucosectomy system including an ablation body with a scaffold located therein.

The illustrative mucosectomy systems of FIGS. 9-11 further include a generally tubular delivery sheath 70 located within an interior of the ablation body 80. In some embodiments, the delivery sheath 70 is preferably located between the proximal end 82 and the distal end 84 of the ablation body 80.

The illustrative mucosectomy systems of FIGS. 9-11 also include a scaffold 60 that is preferably restrained within an interior of the delivery sheath 70. The scaffold 60 may preferably be expandable to a deployed configuration when not restrained by the delivery sheath 70. The scaffold 60 preferably has a diameter in its deployed configuration that is larger than its diameter when restrained within the delivery sheath 70.

The scaffold 60 may be in the form of, e.g., a stent and may be manufactured using materials and/techniques that are used for stents and similar articles (e.g., vascular grafts, etc.).

The use of scaffolds and similar devices may be described in, e.g., U.S. Patent Publication Nos. US 2003/0129751 (Grikscheit et al.); US 2004/0249343 (Cionta); US 2005/0013870 (Freyman et al.); US 2005/0287320 (Dalton et al.); US 2007/0166396 (Badylak et al.); and US 2008/0275550 (Kheradvar et al.); as well as in International Publication No. WO 2006/122414 (Freier et al.). Further approaches that may be used in connection with the scaffolds described herein may be found in Nieponice et al., *An extracellular matrix scaffold for esophageal stricture prevention after circumferential EMR*, Gastrointestinal Endoscopy, 69:2 (2009); Nakase et al., *Intrathoracic esophageal replacement by in situ tissue-engineered esophagus*, The Journal of Thoracic and Cardiovascular Surgery, p. 850 (October 2008); Saito et al., *Usefulness of biodegradable stents constructed of poly-/-lactic acid monofilaments in patients with benign esophageal stenosis*, World J. Gastroenterol. 13(29): 3977-3980 (Aug. 7, 2007); and Rajan et al., *Widespread Endoscopic Mucosal Resection of the Esophagus with Strategies for Stricture Prevention: A Preclinical Study*, Endoscopy 2005; 37 (11): 111-1115.

The illustrative embodiments of the mucosectomy system depicted in FIGS. 10 and 11 are provided to demonstrate that the longitudinal length of the scaffold 60 can vary. For example, the scaffold 60 and its corresponding delivery sheath 70 are shorter than the scaffold 160 contained within delivery sheath 170 in the embodiment of FIG. 11. In some embodiments, it may be preferred to match the length of the scaffold to the length over which the ablation electrodes extend on the ablation body. For example, the scaffold 60 of the embodiment depicted in FIG. 10 is shorter and the ablation electrodes 90 occupy a shorter section of the ablation body 80 as compared to the longer scaffold 160 of FIG. 11 and the corresponding longer section of ablation body 180 occupied by ablation electrodes 190.

In some embodiments, it may be preferred that the scaffold 60 be electrically isolated from the electrical energy delivered to the ablation electrodes 90 when the scaffold 60 is restrained within the delivery sheath 70. Electrical isolation of the scaffold 60 from the energy delivered using the ablation electrodes 90 may assist in preserving the efficacy and/or viability of any treatments delivered using the scaffold 60.

Figure 12:
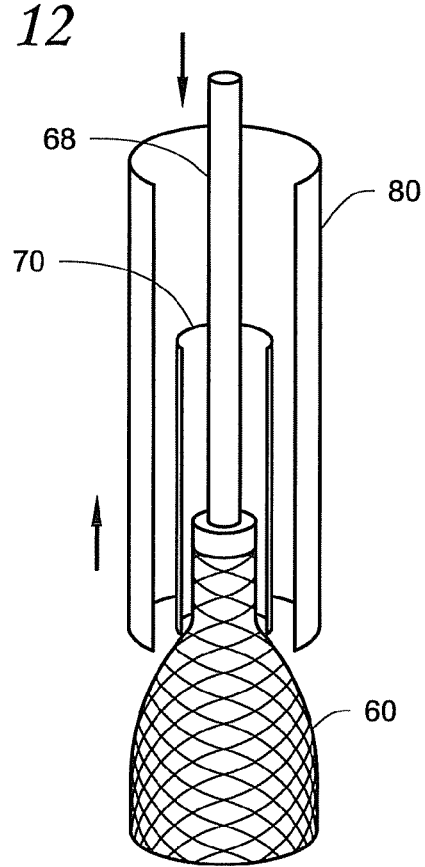
FIG. 12 depicts the esophageal mucosectomy system of FIG. 11 during deployment of the scaffold located in the ablation body.

Referring to FIG. 12, some embodiments of the mucosectomy systems depicted in FIGS. 9-13 may include an ejection apparatus 68 that ejects the scaffold 60 from the delivery sheath 70 such that scaffold 60 can be ejected from the delivery sheath 70 as the ablation body 80 is withdrawn proximally. The ejection apparatus 68 may be in the form of a device capable of pushing on the scaffold 60 (e.g., a plunger or piston-like device).

Figure 13:
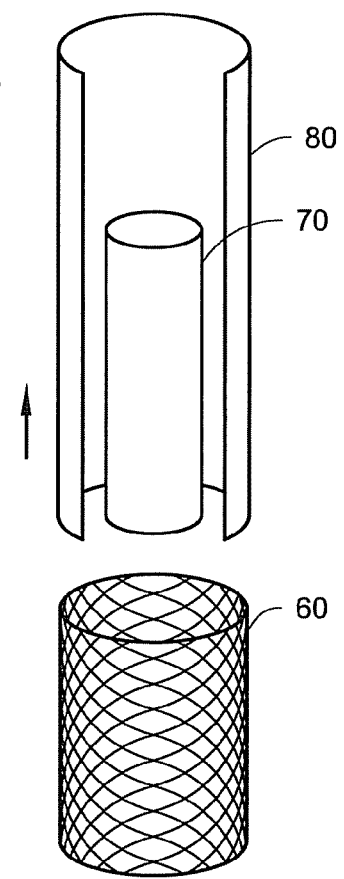
FIG. 13 depicts the esophageal mucosectomy system of FIG. 12 after deployment of the scaffold from the ablation body.

As seen in FIGS. 12-13, the scaffold 60 preferably restrained within the interior of the delivery sheath 70. The scaffold 60 may preferably expand to a deployed configuration as it exits from and is no longer restrained by the delivery sheath 70. The scaffold 60 preferably has a diameter in its deployed configuration (see, e.g., FIG. 13) that is larger than its diameter when restrained within the delivery sheath 70 (see, e.g., FIGS. 10-12).

One illustrative method of using the embodiments of mucosectomy systems described in connection with FIGS. 9-13 may involve the following procedures. An overtube may be located in the patient's esophagus. The overtube may be coupled with a mouthguard/bite block as is known in the art. An endoscope may be introduced through the overtube to allow for visualization and measurement of features in the esophagus.

If the ablation body of the mucosectomy system is too large to fit through a channel of the endoscope, the endoscope may be removed to place the ablation body in the esophagus. Proper placement of the ablation body may be confirmed using, e.g., fluoroscopy. If the ablation body is small enough to be advanced through the overtube or the endoscope, then removal of the endoscope from the overtube may not be required to position the ablation body in the esophagus.

With the ablation body in position in the esophagus, it may be expanded if needed for the electrodes to properly contact the mucosal tissue of the esophagus. Ablation of the selected mucosal tissue can then be performed by delivering electrical energy to the ablation electrodes on the ablation device. In embodiments in which the scaffold is contained within a delivery tube in the ablation body, the scaffold may preferably be insulated from the electrical energy delivered to perform the ablation.

With the ablation complete, the scaffold may be removed from its delivery tube and preferably expanded such that the scaffold contacts the interior surfaces of the esophagus. As discussed herein, the scaffold may carry tissue and/or medication to promote healing and/or reduce the likelihood of stricture in the areas where the mucosal tissue lining the esophagus was ablated.

In some embodiments, the scaffold may be constructed of materials that biodegrade over time (e.g., hours, days, weeks, months, etc.). In other embodiments, the scaffold may include a structure that may be removed after healing has progressed sufficiently.

The complete disclosure of the patents, patent documents, and publications cited in herein are incorporated by reference in their entirety as if each were individually incorporated.

Illustrative embodiments of mucosectomy systems, devices, and apparatus are discussed and reference has been made to possible variations of the same. These and other variations and modifications will be apparent to those skilled in the art without departing from the scope of the invention, and it should be understood that this invention is not limited to the illustrative embodiments set forth herein. Accordingly, the invention is to be limited only by the claims provided below and equivalents thereof.

What is claimed is:

1. An esophageal mucosectomy system comprising:
    a dissection device configured to dissect mucosal tissue in circumferential direction at a selected location within an esophagus, wherein the dissected mucosal tissue forms a free end of mucosal tissue separated from submucosal tissue;
    a mucosectomy device comprising:
        a body having a proximal end and distal end, wherein a longitudinal axis extends between the proximal end and the distal end,
        a cauterizing ring located at the distal end of the body, the cauterizing ring capable of separating mucosal tissue from submucosal tissue about the entire circumference of the esophagus as the distal end of the mucosectomy device is advanced therethrough,
        an expandable support structure supporting the cauterizing ring, wherein the support structure is expandable from a delivery configuration to a deployed configuration, wherein the diameter of the cauterizing ring is larger in the deployed configuration than in the delivery configuration, and further wherein the body of the mucosectomy device is narrower at the proximal end than at the support structure when the support structure is in the deployed configuration, and further wherein the cauterizing ring defines an opening when the support structure is in the deployed configuration, wherein the longitudinal axis extends through the opening when the support structure is in the deployed configuration; and
    a mucosal tissue retention apparatus comprising one or more connectors configured to retain the free end of mucosal tissue and one or more elongate elements attached to the one or more connectors, wherein the one or more elongate elements extend along the longitudinal axis through the opening defined by the cauterizing ring when the support structure is in the deployed configuration.

2. A system according to claim 1, wherein at least one elongate element of the one or more elongate elements of the mucosal tissue retention apparatus comprises a suture line.

3. A system according to claim 1, wherein at least one connector of the one or more connectors of the mucosal tissue retention apparatus comprises a tissue clip.

4. A system according to claim 1, wherein the cauterizing ring of the mucosectomy device comprises two or more independent cauterizing sections, wherein cauterizing energy can be selectively delivered to one or more of the cauterizing sections.

5. A system according to claim 1, wherein the mucosectomy device further comprises a delivery port located proximal the distal end of the mucosectomy device, wherein the delivery port is in fluid communication with a lumen that extends to the proximal end of the mucosectomy device, whereby a fluid can be delivered through the lumen to the delivery port where it exits the mucosectomy device.

6. A system according to claim 1, wherein the support structure of the mucosectomy device comprises an inflatable bladder.

7. A system according to claim 1, wherein the support structure of the mucosectomy device comprises a coiled ring.

8. A system according to claim 1, wherein the support structure of the mucosectomy device comprises a plurality of panels, wherein each panel of the plurality of panels comprises a cauterizing surface at a distal end of the panel.

9. A system according to claim 1, wherein the system further comprises a scaffold located over an exterior surface of the body of the mucosectomy device, wherein the scaffold comprises a distal end that is located proximal from the distal end of the mucosectomy device, and wherein the scaffold is expandable from a delivery configuration to a deployed configuration, wherein the diameter of the scaffold is larger in the deployed configuration than in the delivery configuration.

10. A system according to claim 9, wherein the support structure is collapsible from the deployed configuration to a removal configuration, wherein the diameter of the support structure is smaller in the collapsed configuration than in the deployed configuration, and further wherein the scaffold comprises an internal passage in its deployed configuration that is larger than the support structure in its collapsed configuration such that the distal end of the mucosectomy device can be withdrawn proximally through the internal passage of the scaffold when the support structure is in its collapsed configuration.

11. A system according to claim 1, wherein the mucosal tissue retention apparatus is configured to apply a tensile force to the dissected mucosal tissue.

12. An esophageal mucosectomy system comprising:
 a dissection device configured to dissect mucosal tissue in circumferential direction at a selected location within an esophagus, wherein the dissected mucosal tissue forms a free end of mucosal tissue separated from submucosal tissue;
 a mucosectomy device comprising:
  a body having a proximal end and distal end, wherein a longitudinal axis extends between the proximal end and the distal end,
  a cauterizing ring located at the distal end of the body, the cauterizing ring capable of separating mucosal tissue from submucosal tissue about the entire circumference of the esophagus as the distal end of the mucosectomy device is advanced therethrough,
  an expandable support structure supporting the cauterizing ring, wherein the support structure is expandable from a delivery configuration to a deployed configuration, wherein the cauterizing ring is larger in the deployed configuration than in the delivery configuration, further wherein the body of the mucosectomy device is narrower at the proximal end than at the support structure when the support structure is in the deployed configuration, and further wherein the cauterizing ring defines an opening when the support structure is in the deployed configuration, wherein the longitudinal axis extends through the opening when the support structure is in the deployed configuration; and
 a mucosal tissue retention apparatus comprising one or more connectors configured to retain the free end of mucosal tissue and one or more elongate structures attached to the one or more connectors, wherein the one or more elongate elements extend along the longitudinal axis through the opening defined by the cauterizing ring when the support structure is in the deployed configuration, and wherein the one or more elongate structures are configured to apply a tensile force to the dissected mucosal tissue.

13. A system according to claim 12, wherein at least one elongate structure of the one or more elongate structures of the mucosal tissue retention apparatus comprises a suture line.

14. A system according to claim 12, wherein at least one connector of the one or more connectors of the mucosal tissue retention apparatus comprises a tissue clip.

15. A system according to claim 12, wherein the cauterizing ring of the mucosectomy device comprises two or more independent cauterizing sections, wherein cauterizing energy can be selectively delivered to one or more of the cauterizing sections.

16. A system according to claim 12, wherein the mucosectomy device further comprises a delivery port located proximal the distal end of the mucosectomy device, wherein the delivery port is in fluid communication with a lumen that extends to the proximal end of the mucosectomy device, whereby a fluid can be delivered through the lumen to the delivery port where it exits the mucosectomy device.

17. A system according to claim 12, wherein the support structure of the mucosectomy device comprises an inflatable bladder.

18. A system according to claim 12, wherein the support structure of the mucosectomy device comprises a coiled ring.

19. A system according to claim 12, wherein the support structure of the mucosectomy device comprises a plurality of panels, wherein each panel of the plurality of panels comprises a cauterizing surface at a distal end of the panel.

20. A system according to claim 12, wherein the system further comprises a scaffold located over an exterior surface of the body of the mucosectomy device, wherein the scaffold comprises a distal end that is located proximal from the distal end of the mucosectomy device, and wherein the scaffold is expandable from a delivery configuration to a deployed configuration, wherein the scaffold is larger in the deployed configuration than in the delivery configuration.

* * * * *